United States Patent
Hashimoto et al.

(10) Patent No.: US 6,638,538 B1
(45) Date of Patent: Oct. 28, 2003

(54) HYALURONIC ACID GEL COMPOSITION, PROCESS FOR PRODUCING THE SAME, AND MEDICAL MATERIAL CONTAINING THE SAME

(75) Inventors: Masamichi Hashimoto, Tokyo (JP); Toshihiko Umeda, Tokyo (JP); Kazuhiko Arai, Niigata (JP); Yoshiaki Miyata, Tokyo (JP); Osamu Yamamoto, Tokyo (JP); Yasukazu Himeda, Tokyo (JP)

(73) Assignee: Denki Kagaku Kogyo Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/913,718

(22) PCT Filed: Feb. 18, 2000

(86) PCT No.: PCT/JP00/00946

§ 371 (c)(1),
(2), (4) Date: Sep. 27, 2001

(87) PCT Pub. No.: WO00/49084

PCT Pub. Date: Aug. 24, 2000

(30) Foreign Application Priority Data

Feb. 19, 1999 (JP) .............................................. 11-42371
Nov. 9, 1999 (JP) ........................................... 11-318579

(51) Int. Cl.[7] .............................................. A61K 35/34

(52) U.S. Cl. ........................ 424/548; 424/445; 514/781; 524/29

(58) Field of Search ........................... 524/29; 514/781; 424/548, 445

(56) References Cited

U.S. PATENT DOCUMENTS

| 4,582,865 A | * | 4/1986 | Balazs et al. ................ 514/781 |
| 5,346,935 A | | 9/1994 | Suzuki et al. .................. 524/18 |
| 6,387,413 B1 | | 5/2002 | Miyata et al. ............... 424/548 |

FOREIGN PATENT DOCUMENTS

| EP | 0 544 259 | 6/1993 |
| JP | 3-215417 | 9/1991 |
| JP | 5-58881 | 3/1993 |
| JP | 9-10294 | 1/1997 |
| JP | 10-290830 | 11/1998 |

* cited by examiner

Primary Examiner—Thurman K. Page
Assistant Examiner—Konata M. George
(74) Attorney, Agent, or Firm—Oblon, Spivak, McClelland, Maier & Neustadt, P.C.

(57) ABSTRACT

A hyaluronic acid gel composition comprising hyaluronic acid and a polymer, which is substantially unmodified with a chemical cross-linking agent or a chemical modifying agent and which has a percentage dissolution of hyaluronic acid of 50% or lower in 12 hours in a neutral aqueous solution of 37° C.

31 Claims, No Drawings

HYALURONIC ACID GEL COMPOSITION, PROCESS FOR PRODUCING THE SAME, AND MEDICAL MATERIAL CONTAINING THE SAME

TECHNICAL FIELD

The present invention relates to a novel hardly water-soluble hyaluronic acid gel composition comprising hyaluronic acid and a polymer, which is substantially unmodified with a chemical cross-linking agent or a chemical modifying agent, and a process for its production. Further, it relates particularly to a medical material utilizing it and having good biocompatibility.

BACKGROUND ART

Hyaluronic acid is a linear macromolecular polysaccharide consisting of alternately bonded β-D-N-acetylglucosamine and β-D-glucuronic acid, and it is known to have no species or organ specificity and show excellent biocompatibility even when implanted or injected into the body.

Various chemical modifications of hyaluronic acid have been proposed in order to overcome drawbacks of hyaluronic acid in its application in vivo as a medical material, such that it is easily soluble in water and its in vivo residence time is relatively short. Further, many hyaluronic acid compositions have been studied for modification by an addition of a polymer to supplement various physical properties required for a medical material such as the strength and tissue bondability.

For example, in order to use a hyaluronic acid composition as a bone-repairing material, a higher strength is required as compared with a case where it is used for an artificial cartilage for a joint. Likewise, when a hyaluronic acid composition is used as an adhesion preventive, a higher tissue bondability is required as compared with a case where it is used as an embolizing agent.

Heretofore, a hyaluronic acid composition useful as a medical material may, for example, be a hyaluronic acid composition having sodium hyaluronate and carboxymethyl cellulose, modified with EDC (1-ethyl-3-(3-dimethylaminopropyl)carbodiimide hydrochloride) as a carbodiimide, as reported in e.g. JP-A-5-508161 and JP-A-6-508169. Further, W086/00912 reports on a hyaluronic acid composition having a carboxy-containing polysaccharide (such as sodium hyaluronate, carboxymethyl dextran, carboxymethyl starch or carboxymethyl cellulose) cross-linked with e.g. BDDE (1,4-butanediol glycine ether) as a di- or poly-functional epoxide. Further, JP-A-61-164558 reports on a hyaluronic acid composition having sodium hyaluronate, chondroitin sulfate, heparin or the like cross-linked with a polyfunctional epoxide, or with cyan bromide, epichlorohydrin or the like. Further, JP-A-61-138601 reports on a hyaluronic acid composition having sodium hyaluronic acid or various polymers cross-linked with divinylsulfone. Further, JP-A-6-73102 and JP-A-8-301903 report on a hyaluronic acid composition having sodium hyaluronate or various polymers cross-linked with cinnamic acid.

However, in their production, it is very difficult to completely remove the cross-linking agent, etc. for purification. Not only that, hyaluronic acid and polymers are likely to include such a cross-linking compound in the molecules, and their physiological functions, biocompatibility and safety can not hardly be said to be substantially equivalent to hyaluronic acid and the polymers.

A hyaluronic acid composition which employs no chemical cross-linking agent or no chemical modifying agent in order to maximize the excellent characteristics of biocompatibility inherent to hyaluronic acid and the polymer itself and which is useful as a biocompatible medical material and has a long in vivo residence time, has not yet been developed.

In order to accomplish the above object, the present inventors have strenuously studied the physiochemical properties of a hyaluronic acid gel (PCT/JP98/03536) itself employing no chemical cross-linking agent or no chemical modifying agent, which is composed solely of hyaluronic acid and which is excellent in biocompatibility and moldability and has an in vivo degradable nature.

Further, they have found that a hyaluronic acid gel composition comprising hyaluronic acid and a polymer, which is substantially unmodified with a chemical cross-linking agent or a chemical modifying agent, will supplement the inherent properties of a hyaluronic acid gel such as strength, adhesiveness, viscosity and elasticity and also will satisfy the physical properties required for a medical material which can hardly be satisfied by a hyaluronic acid gel alone, and it can simply be prepared and has ideal biocompatibility and retention property as a medical material, and they have arrived at the present invention.

Especially when carboxymethyl cellulose is employed as the polymer of this hyaluronic acid gel composition, the composition is particularly suitable as an adhesion preventive or a wound dressing.

DISCLOSURE OF THE INVENTION

Namely, the present invention is (1) a hyaluronic acid gel composition comprising hyaluronic acid and a polymer, which is substantially unmodified with a chemical cross-linking agent or a chemical modifying agent and which has a percentage dissolution of hyaluronic acid of 50% or lower in 12 hours in a neutral aqueous solution of 37° C., (2) the hyaluronic acid gel composition according to (1), wherein the polymer is carboxymethyl cellulose, (3) a process for producing a hyaluronic acid gel composition, which comprises freezing an aqueous solution or dispersion containing hyaluronic acid and a polymer and having a pH of 3.5 or lower, followed by unfreezing to form a hyaluronic acid gel composition, (4) a process for producing a hyaluronic acid gel composition, which comprises freezing an aqueous solution containing hyaluronic acid and having a pH of 3.5 or lower, followed by unfreezing to form a hyaluronic acid gel, and mixing the hyaluronic acid gel with a polymer or a polymer gel to form a hyaluronic acid gel composition, (5) the process for producing a hyaluronic acid gel composition according to (3) or (4), wherein the polymer is at least one member selected from the group consisting of polysaccharides, proteins, nucleic acids and synthetic polymers, (6) the process for producing a hyaluronic acid gel composition according to (3) or (4), wherein the polymer is carboxymethyl cellulose, (7) a medical material containing the hyaluronic acid gel composition as defined in (1) or (2), (8) a medical material containing a hyaluronic acid gel composition which is obtained by irradiating or injecting one member selected from the group consisting of gamma rays, electron rays, plasma or EOG to a hyaluronic acid gel composition, (9) the medical material according to (7), wherein the material is an adhesion preventive, and (10) the medical material according to (7), wherein the medical material is a wound dressing.

BEST MODE FOR CARRYING OUT THE INVENTION

Now, the present invention will be described in detail.

In the present invention, modification means cross-linking or chemical modification to make naturally water-soluble hyaluronic acid or polymer to be hardly soluble.

The hyaluronic acid gel composition of the present invention can be obtained by freezing an aqueous solution or dispersion having a pH of 3.5 or lower containing hyaluronic acid and a polymer, followed by unfreezing and by neutralization, washing and drying.

Further, the hyaluronic acid gel composition of the present invention can be obtained by freezing an aqueous solution containing hyaluronic acid and having a pH of 3.5 or lower, followed by unfreezing to obtain a hyaluronic acid gel, which is then pulverized and put, together with a polymer gel, into an aqueous solution such as water, followed by pulverization, dispersion and drying.

With these hyaluronic acid gel compositions, the mechanical strength and the tissue bondability can simply be improved as compared with a case of the hyaluronic acid gel alone.

Any acid may be used as the acid to be employed to adjust the pH of the aqueous solution of hyaluronic acid and the polymer, so long as it is an acid capable of adjusting the pH to a level of 3.5 or lower. In order to reduce the amount of the acid, it is preferred to use a strong acid such as hydrochloric acid, nitric acid or sulfuric acid.

For freezing and unfreezing, an operation wherein a acidic aqueous solution having hyaluronic acid and a polymer adjusted, is put into an optional container and then frozen at a predetermined temperature, and after completion of the freezing, unfreezing is carried out at a predetermined temperature, at least once. The temperatures and the times for freezing and unfreezing may suitably be determined within ranges of the temperatures and the times for freezing and unfreezing of the acidic aqueous solution of hyaluronic acid, depending upon the size of the container and the amount of the aqueous solution. However, usually, a freezing temperature of lower than the freezing point and an unfreezing temperature of higher than the freezing point, are preferred. Since the freezing and unfreezing times can be shortened, a freezing temperature of −5° C. or lower and an unfreezing temperature of 5° C. or higher are selected more preferably. Further, the times are not particularly limited so long as they are sufficient to complete the freezing and the unfreezing at the respective temperatures.

The number of repetitions of the operation of freezing the acidic aqueous solution having hyaluronic acid and the polymer adjusted, followed by unfreezing, is suitably determined depending upon the molecular weight of hyaluronic acid to be used, the concentration of the aqueous solution, the pH of the aqueous solution, the temperatures and times of the freezing and unfreezing, and various properties such as strength of the hyaluronic acid gel composition to be formed. Usually, it is preferred to repeat the operation at least once.

Every time when the operation of freezing and unfreezing is repeated, the temperatures and the times for the freezing and unfreezing may be changed.

With respect to treatment such as molding of the hyaluronic acid gel composition, at the time of preparation, by selection of a method or a container for freezing the acidic solution having hyaluronic acid adjusted, it is possible to prepare a hyaluronic acid gel composition in a desired form such as a sheet-form, a film-form, a pulverized form, a sponge-form, a bulk form, a fiber-form, a fluid-form or a tube-form.

For example, a hyaluronic acid gel composition of a sheet-form can be obtained by putting the hyaluronic acid composition or its dispersion in a container having a flat bottom, followed by freeze drying.

Further, a hyaluronic acid gel composition of a film-form can be obtained by putting the hyaluronic acid composition or its dispersion in a container having a flat bottom, followed by drying in air.

Hyaluronic acid to be used in the present invention may be one extracted from an animal tissue, or one produced by a fermentation method, and it may be used irrespective of its origin.

The molecular weight of hyaluronic acid to be used in the present invention is preferably one within a range of from about $1 \times 10^5$ to about $1 \times 10^7$ Da. Further, so long as it is one having a molecular weight within the above range, even one obtained from one having a higher molecular weight by e.g. hydrolytic treatment, may likewise preferably be used.

Further, in the present invention, hyaluronic acid is used in a concept which includes also an alkali metal salt such as a sodium, potassium or lithium salt.

As the polymer to be used in the present invention, it is possible to use any polymer which is capable of forming a hyaluronic acid gel composition of the present invention irrespective of a natural polymer or a synthetic polymer, and any polymer which is capable of supplementing the inherent properties of the hyaluronic acid gel for the physical properties required for a medical material which can hardly be satisfied by the hyaluronic acid gel alone.

Accordingly, all polymers which will be taken into a hyaluronic acid gel without being involved in formation of cross-linking among polymers themselves or between a polymer and a hyaluronic acid gel and which are capable of forming a hyaluronic acid gel composition of the present invention, can be used for the present invention.

Typical examples of the polymer to be used in the present invention are selected from the group consisting of polysaccharides, proteins, nucleic acids and synthetic polymers, but the useful polymer is not limited thereto.

Examples of polysaccharides may be glycosaminoglycans (such as heparin, heparan sulfate and dermatan sulfate), chondroitin sulfates (such as chondroitin-6-sulfate), keratin sulfates, heparan sulfates, alginic acid and its biologically acceptable salts, cellulose, chitin, chitosan, dextran, starch, amylose, polyactic acid and calaginan.

Further, synthetic derivatives of polysaccharides may, for example, be carboxymethyl cellulose, carboxymethyl amylose, various alkyl celluloses, hydroxyethyl cellulose, carboxy cellulose and oxidized starch and oxidized regenerated cellulose.

Further, examples of proteins may be collagen, gelatin, albumin, elastin, various globulins, casein, gluten, and their biologically acceptable synthetic derivatives.

Further, examples of the synthetic polymer may be polyvinyl alcohol, polyethylene glycol, polyglycolic acid, polyacrylic acid, polymethacrylic acid, copolymers thereof, and derivatives such as poly(hydroxyethyl)acrylates or methacrylates, polyacrylamides, polyvinyl alcohols and copolymers of maleic acid or fumaric acid.

Further, the present invention is by no means restricted to these polymers.

The aqueous solution or dispersion containing hyaluronic acid and a polymer and having a pH of 3.5 or lower, to be used in the present invention, can be obtained by mixing and stirring hyaluronic acid and a polymer with water. The concentrations of hyaluronic acid and the polymer are preferably 5.0 mass % or lower, respectively, from the viewpoint of handling efficiency of the aqueous solution or dispersion.

Especially when hyaluronic acid having a molecular weight of $2\times10^6$ Da or higher, is used, the concentration of the hyaluronic acid is preferably 2.5 mass % or lower. The blend ratio of the aqueous solution or dispersion containing hyaluronic acid and a polymer and having a pH of 3.5 or lower, is not particularly limited, so long as a hyaluronic acid gel composition can be obtained by freezing and unfreezing this liquid. For example, the blend ratio as an adhesion preventive, is preferably from 50:1 to 1:20.

Further, in the present invention, a hyaluronic acid gel and a polymer gel may be prepared separately, and they may be pulverized to obtain a hyaluronic acid gel pulverized product and a polymer gel pulverized product, and such pulverized products may be mixed to obtain a hyaluronic acid gel composition.

The ratio of mixing the hyaluronic acid gel and the polymer gel to be used in the present invention is not particularly limited so long as the mixture can be put into an aqueous solution such as water and can be pulverized and dispersed.

The hyaluronic acid gel composition obtained by the present invention may be used without any particular restriction as a general biodegradable biomedical material in any fields wherein hyaluronic acid is used. It may be used for, e.g. an adhesion preventive, an artificial cartilage for a joint, a carrier for a pharmacologically active substance, a wound dressing, an artificial skin, a replacement vital tissue repairer, a joint injection, a surgical suture, a hemostatic material, an artificial organ, an artificial extracellular matrix, an artificial basement membrane or biomedical products such as medical tools and devices for diagnostic or therapeutic use or medicinal compositions. Further, it is possible to obtain a hyaluronic acid gel composition containing a physiologically active substance by mixing the physiologically active substance when the hyaluronic acid gel and the polymer gel are mixed.

Then, a medical material obtained by irradiation treatment of the hyaluronic acid gel composition of the present invention, will be described. The γ-rays to be irradiated to the hyaluronic acid gel composition are preferably produced from cobalt 60 or cesium 137 as a radiation source. When γ-rays having a dose of 30 kGy or lower are preferably irradiated to a dried product of the hyaluronic acid gel composition, a hyaluronic acid gel composition effective for an adhesion preventive or a wound treating agent, can be obtained. Further, by changing the irradiation dose or the irradiation time, the solubility of the hyaluronic acid gel composition can be controlled, and it is possible to control a proper in vivo retention property in an application as a biological material. A sterilization effect is also expected by irradiation of γ-rays to the hyaluronic acid gel composition.

Electron rays to be irradiated to the hyaluronic acid gel composition are generated by an electron ray accelerator. When electron rays having a dose of 30 kGy or lower are preferably irradiated to a dry product of the hyaluronic acid gel composition, a hyaluronic acid gel composition effective for an adhesion preventive or a wound dressing, can be obtained.

Plasma is represented as the fourth state of substance distinguishable from solid, liquid and gas, and it usually comprises ions, electrons and neutral nuclear species. The gas ionized by applying an electric power to the gas stream, is known also as glow discharge.

As the plasma to be irradiated to the hyaluronic acid gel composition, a low temperature gas plasma to be formed by exposing a mixture of hydrogen, oxygen and an inert carrier gas to an electromagnetic field, may, for example, be used.

A dried product of the hyaluronic acid gel composition is put in a chamber of a plasma generator, and a plasma-generating gas comprising argon, oxygen and hydrogen, is injected and dispersed and then irradiated in a plasma atmosphere for at least 10 minutes, whereby a hyaluronic acid gel composition effective for an adhesion preventive or a wound dressing, can be obtained.

EOG is usually a sterilization method employing ethylene oxide gas, which is applied to a material which can not be subjected to dry sterilization or vapor sterilization. A dried product of the hyaluronic acid gel composition is put into an EOG sterilization chamber, EOG is then injected, and sterilization is carried out preferably at a temperature of 50° C. or lower, such being effective for an adhesion preventive or a wound dressing.

By changing the temperature or the time for injecting EOG, the solubility of the hyaluronic acid gel composition can be controlled, and it is possible to control a proper in vivo retention property in its application as a biological material.

Now, an adhesion preventive among medical materials of the present invention will be described.

The adhesion preventive made of a hyaluronic acid gel composition obtained according to the present invention is a sheet-like, filmy, flaky, spongy, massive, fibrous, fluid-form or tubular material for surgical use. With respect to the mode of use, it is preferred to directly apply a filmy or sheet-like material to a part subjected to surgery. It is also preferred to apply a fine flaky or fluid-form material by injection to a part subjected to surgery. It is also useful for peritoneoscopical surgery.

Further, an adhesion preventive made of a hyaluronic acid gel composition encapsulating a physiologically active compound can be obtained by mixing a prepared acidic hyaluronic acid gel composition solution and a physiologically active compound and then freezing and unfreezing the mixture.

The adhesion preventive made of a hyaluronic acid gel composition obtained according to the present invention may be administered at any time during or after the operation so long as postoperative adhesion can be prevented, but preferably immediately before the completion of the operation.

EXAMPLES

Now, the present invention will be described in further detail with reference to Examples. However, the present invention is by no means restricted to these specific Examples.

Example 1

Sodium hyaluronate having a molecular weight of $2\times10^6$ Da and sodium carboxymethyl cellulose (manufactured by Wako Pure Chemical Industries, Ltd.) were dissolved in distilled water so that each became 0.5 mass %. The pH of the prepared aqueous solution was adjusted with 1 mol/l hydrochloric acid to pH 1.5. 15 ml of the acidic aqueous solution was put into a glass bottle of 30 ml and placed in a freezer set at −20° C. It was left to stand for 5 days, and then unfreezed at 25° C. As a result, a spongy hyaluronic acid gel composition was obtained.

Example 2

Sodium hyaluronate having a molecular weight of $2\times10^6$ Da and polyvinyl alcohol (polymerization degree: 1,500, manufactured by Wako Pure Chemical Industries, Ltd.) were dissolved in distilled water so that they were 0.5 mass % and 10 mass %, respectively. The pH of the prepared aqueous solution was adjusted with 1 mol/l hydrochloric acid to pH 1.5. 15 ml of the acidic aqueous solution was put into a glass bottle of 30 ml and placed in a freezer set at −20° C. It was left to stand for 5 days, and then unfreezed at 25° C. As a result, a block-shape hyaluronic acid gel composition was obtained.

Example 3

Sodium hyaluronate having a molecular weight of $2\times10^6$ Da and sodium arginate (manufactured by Funakoshi K.K.) were dissolved in distilled water so that each became 0.5 mass %. The pH of the prepared aqueous solution was adjusted with 1 mol/l hydrochloric acid to pH 1.5. 15 ml of the acidic aqueous solution was put into a glass bottle of 30 ml and placed in a freezer set at −20° C. It was left to stand for 5 days, and then unfreezed at 25° C. As a result, a spongy hyaluronic acid gel composition was obtained.

Comparative Example 1

In Example 1, the pH of the mixed aqueous solution was not adjusted, and freezing and unfreezing were repeated 8 times in a neutral state. As a result, no change of the aqueous solution of hyaluronic acid was observed. Namely, it was not gelled. After the 9th freezing, freeze-drying was carried out to obtain a spongy hyaluronic acid composition.

Comparative Example 2

In Example 2, without adjusting the pH of the mixed aqueous solution, freezing and unfreezing were repeated 8 times in a neutral state. As a result, no change of the aqueous solution of hyaluronic acid took place. Namely, it was not gelled. After the 9th freezing, freeze-drying was carried out to obtain a spongy hyaluronic acid composition.

Comparative Example 3

In Example 3, without adjusting the pH of the mixed aqueous solution, freezing and unfreezing were repeated 8 times in a neutral state. As a result, no change of the aqueous solution of hyaluronic acid took place. Namely, it was not gelled. After the 9th freezing, freeze-drying was carried out to obtain a spongy hyaluronic acid composition.

Reference Example 1

Sodium hyaluronate having a molecular weight of $2\times10^6$ Da was dissolved in distilled water so that it became 1.0 mass %. The pH of the prepared aqueous solution was adjusted with 1 mol/l hydrochloric acid to pH 1.5. 15 ml of the acidic aqueous solution was put into a glass bottle of 30 ml and placed in a freezer set at −20° C. It was left to stand for 5 days, and then unfreezed at 25° C. As a result, a spongy hyaluronic acid gel was obtained.

Example 4
Solubility tests of the hyaluronic acid gel compositions

A phosphate buffer component was added to physiological saline at a concentration of 50 mmol/l to obtain a phosphate-buffered physiological saline of pH 7. The spongy hyaluronic acid gel compositions obtained in the preceding Examples 1 to 3 and hyaluronic acid gel obtained in Reference Example 1, were washed with distilled water and drained on filter paper. The hyaluronic acid gel compositions were immersed in the phosphate-buffered physiological saline in such a proportion that the obtained hyaluronic acid gel compositions containing 150 ml by dry weight of hyaluronic acid were in 50 ml of the phosphate-buffered physiological saline. Further, the freeze-dried spongy hyaluronic acid compositions containing 150 ml by dry weight of hyaluronic acid obtained in the preceding Comparative Examples 1 to 3, were immersed in the phosphate-buffered physiological saline in such a proportion that the hyaluronic acid compositions were in 50 ml of the phosphate-buffered physiological saline.

Then, the solubilities of the hyaluronic acid gel compositions and the hyaluronic acid compositions were visually determined. Further, the proportion of hyaluronic acid eluted into the phosphate-buffered physiological saline at 25° C., was obtained from the hyaluronic acid concentration in the phosphate-buffered physiological saline.

Accordingly, the solubility of a hyaluronic acid gel composition in a neutral aqueous solution at 25° C. is one stipulated by the above test. Measurement of hyaluronic acid concentration Hyaluronic acid in the phosphate-buffered physiological saline, was measured by means of GPC. Hyaluronic acid has a high molecular weight and thus elutes first, and carboxymethyl cellulose or polyvinyl alcohol having a low molecular weight elutes thereafter. The concentration of hyaluronic acid was obtained from a peak area of the peak of hyaluronic acid thus eluted, as measured by a differential refractometer.

As described above, the solubility tests of the hyaluronic acid gel compositions of Examples 1 to 3 and the hyaluronic acid gel of Reference Example 1, and the hyaluronic acid compositions of Comparative Examples 1 to 3, were specifically carried out. The results are shown in Table 1.

TABLE 1

| | Percentage dissolution of hyaluronic acid (%) | | | |
|---|---|---|---|---|
| Test No. | One day | 4 days | 10 days | Notes |
| 1 | 2 | 4 | 6 | Ex. 1 |
| 2 | 0 | 1 | 3 | Ex. 2 |
| 3 | 3 | 5 | 10 | Ex. 3 |
| 4 | 100 | 100 | 100 | Comp. Ex. 1 |
| 5 | 100 | 100 | 100 | Comp. Ex. 2 |
| 6 | 100 | 100 | 100 | Comp. Ex. 3 |
| 7 | 3 | 5 | 10 | Ref. Ex. 1 |

From Table 1, for example, the percentage dissolution of the hyaluronic acid gel composition obtained in Example 1 of Test No. 1, is examined, whereby upon expiration of one day, hyaluronic acid had a percentage dissolution of 2%, upon expiration of 4 days, it had a percentage dissolution of 4%, and further upon expiration of 10 days, it had a percentage dissolution of 6%. Namely, even upon expiration of 10 days, 94% of hyaluronic acid remained to be the hyaluronic acid gel. The spongy form was also maintained.

If the percentage dissolution of the hyaluronic acid gel obtained in Reference Example 1 of Test No. 7 is examined, upon expiration of one day, it had a percentage dissolution of 3%, upon expiration of 4 days, it had a percentage dissolution of 5%, and further upon expiration of 10 days, it had a percentage dissolution of 10%. Namely, the percentage dissolutions of the hyaluronic acid gel compositions obtained in Examples 1 to 3 were found to be the same as the percentage dissolutions of the hyaluronic acid gel obtained in Reference Example 1.

Whereas, when the percentage dissolutions of the hyaluronic acid compositions obtained in Comparative Examples 1 to 3 of Test No. 4 to 6 are examined, upon expiration of one day, the percentage dissolutions were 100%, and the compositions were completely dissolved.

Example 5
Solubility tests of hyaluronic acid gel compositions

A phosphate buffer component was added to physiological saline at a concentration of 50 mmol/l to obtain a phosphate-buffered physiological saline of pH 7. The spongy hyaluronic acid gel compositions obtained in the preceding Examples 1 to 3 and hyaluronic acid gel obtained in Reference Example 1 were washed with distilled water and drained on filter paper. The hyaluronic acid gel compositions were immersed in the phosphate-buffered physiological saline in such a proportion that the obtained hyaluronic acid gel compositions containing 20 mg by dry weight of hyaluronic acid were in 50 ml of the phosphate-buffered physiological saline. Further, the freeze-dried spongy hyaluronic acid compositions containing 20 mg by dry weight of hyaluronic acid, obtained in the preceding Comparative Examples 1 to 3, were immersed in the phosphate-buffered physiological saline in such a proportion that the hyaluronic acid compositions were in 50 ml of the phosphate-buffered physiological saline.

Then, the proportion of the hyaluronic acid eluting into the phosphate-buffered physiological saline with stirring at 37° C., was obtained from the hyaluronic acid concentration in the phosphate-buffered physiological saline.

Accordingly, the solubility of a hyaluronic acid gel composition in a neutral aqueous solution at 37° C. is one prescribed by the above test.

As described above, the solubility tests of the hyaluronic acid gel compositions of Examples 1 to 3 and the hyaluronic acid gel of Reference Example 1, and the hyaluronic acid compositions of Comparative Examples 1 to 3, were specifically carried out. The results are shown in Table 2.

TABLE 2

| Test No. | Percentage dissolution of hyaluronic acid (%) | | | Notes |
| --- | --- | --- | --- | --- |
| | 6 hours later | 12 hours later | 24 hours later | |
| 8 | 12 | 14 | 18 | Ex. 1 |
| 9 | 10 | 16 | 23 | Ex. 2 |
| 10 | 13 | 15 | 20 | Ex. 3 |
| 11 | 100 | 100 | 100 | Comp. Ex. 1 |
| 12 | 100 | 100 | 100 | Comp. Ex. 2 |
| 13 | 100 | 100 | 100 | Comp. Ex. 3 |
| 14 | 12 | 15 | 20 | Ref. Ex. 1 |

From Table 2, for example, the percentage dissolution of the hyaluronic acid gel composition obtained in Example 1 of Test No. 8, is examined, whereby upon expiration of 6 hours, hyaluronic acid had a percentage dissolution of 12%, upon expiration of 12 hours, it had a percentage dissolution of 14%, and further upon expiration of 24 hours, it had a percentage dissolution of 18%. Namely, even upon expiration of 24 hours, 82% of hyaluronic acid remained to be a hyaluronic acid gel.

When the percentage dissolution of the hyaluronic acid gel obtained in Reference Example 1 of Test No. 14 is examined, upon expiration of 6 hours, the gel had a percentage dissolution of 12%, upon expiration of 12 hours, it had a percentage dissolution of 15%, and further upon experation of 24 hours, it had a percentage dissolution of 20%. Namely, the percentage dissolutions of the hyaluronic acid gel compositions obtained in Examples 1 to 3 were found to be the same as the percentage dissolutions of the hyaluronic acid gel obtained in Reference Example 1.

Whereas, when the percentage dissolutions of the hyaluronic acid compositions obtained in Comparative Examples 1 to 3 of Test No. 10 to 12 are examined, upon expiration of 6 hours, the percentage dissolutions were 100%, and the compositions were completely dissolved.

Example 6

Sodium hyaluronate having a molecular weight of $2\times10^6$ Da and chitosan (manufactured by Wako Pure Chemical Industries, Ltd.) were mixed to distilled water in amounts of 1.0 mass % and 0.1 mass %, respectively, and the pH was adjusted with 1 mol/l hydrochloric acid to pH 1.5. 15 ml of the acidic aqueous solution was put into a glass bottle of 30 ml and placed in a freezer set at −20° C. It was left to stand for 5 days, and then unfreezed at 25° C. As a result, a spongy hyaluronic acid gel composition was obtained.

Example 7
Solubility Tests of Hyaluronic Acid Gel Compositions

A phosphate buffer component was added to physiological saline at a concentration of 100 mmol/l to obtain a phosphate-buffered physiological saline of pH 7. The spongy hyaluronic acid gel compositions obtained in the preceding Examples 1, 2 and 6 were washed with distilled water and drained on filter paper. The hyaluronic acid gel compositions were immersed in the phosphate-buffered physiological saline in such a proportion that the obtained hyaluronic acid gel compositions containing 20 mg by dry weight of hyaluronic acid were in 100 ml of the phosphate-buffered physiological saline.

The proportion of the hyaluronic acid, carboxymethyl cellulose, polyvinyl alcohol and chitosan eluting into the phosphate-buffered physiological saline at 37° C., were obtained from the concentrations of the respective components in the phosphate-buffered physiological saline. Measurement of concentrations of hyaluronic acid, carboxymethyl cellulose, polyvinyl alcohol and chitosan Hyaluronic acid, carboxymethyl cellulose, polyvinyl alcohol and chitosan in the phosphate-buffered physiological saline, were measured by means of GPC. Hyaluronic acid has a high molecular weight and thus elutes first, by GPC, and carboxymethyl cellulose, polyvinyl alcohol and chitosan having a low molecular weights will elute thereafter. The concentration of hyaluronic acid was obtained from the peak area of the peak of hyaluronic acid thus eluted, as measured by a differential refractometer.

As described above, the solubility tests of the hyaluronic acid gel compositions of Examples 1, 2 and 6 were specifically carried out. The results are shown in Table 3.

TABLE 3

| Test No. | Components | Percentage dissolutions of hyaluronic acid, carboxymethyl cellulose, polyvinyl alcohol and chitosan (%) | | | Notes |
| --- | --- | --- | --- | --- | --- |
| | | One day later | 4 days later | 10 days later | |
| 15 | HA | 2 | 4 | 6 | Ex. 1 |
| | CMC | 10 | 30 | 51 | |
| 16 | HA | 0 | 1 | 3 | Ex. 2 |
| | PVA | 0 | 1 | 1 | |
| 17 | HA | 1 | 4 | 6 | Ex. 6 |
| | Chitosan | 4 | 5 | 6 | |

From Table 3, for example, the percentage dissolution of the hyaluronic acid gel composition obtained in Example 1 of Test No. 15, is examined, whereby upon expiration of one day, hyaluronic acid had a percentage dissolution of 2%, upon expiration of 4 days, it had a percentage dissolution of 4%, and further upon expiration of 10 days, it had a percentage dissolution of 6%. Further, upon expiration of one day, carboxymethyl cellulose had a percentage dissolution of 10%, upon expiration of 4 days, it had a percentage dissolution of 30%, and further, upon expiration of 10 days, it had a percentage dissolution of 51%.

When the percentage dissolution of the hyaluronic acid gel composition obtained in Example 2 of Test No. 16 is examined, upon expiration of one day, hyaluronic acid had a percentage dissolution of 0%, upon expiration of 4 days, it had a percentage dissolution of 1%, and further upon expiration of 10 days, it had a percentage dissolution of 3%. Further, upon expiration of one day, polyvinyl alcohol had a percentage dissolution of 0%, upon expiration of 4 days, it had a percentage dissolution of 1%, and further upon expiration of 10 days, it had a percentage dissolution of 1%.

When the percentage dissolution of the hyaluronic acid gel composition obtained in Examples 6 of Test No. 17 is examined, upon expiration of one day, hyaluronic acid had a percentage dissolution of 1%, upon expiration of 4 days, it had a percentage dissolution of 4%, and further upon expiration of 10 days, it had a percentage dissolution of 5%. Further, upon expiration of one day, chitosan had a percentage dissolution of 4%, upon expiration of 4 days, it had a percentage dissolution of 5%, and further upon expiration of 10 days, it had a percentage dissolution of 6%.

Example 8
Test on Cytotoxicity of a Hyaluronic Acid Gel Composition

The cytotoxicity of the hyaluronic acid gel composition obtained according to the present invention was evaluated by observing the proliferation behavior of a normal human skin-derived fibroblast culture in the presence of the hyaluronic acid gel composition obtained according to the present invention without contact between them. The spongy hyaluronic acid gel composition obtained in Example 1 was immersed in the phosphate-buffered physiological saline and then freeze-dried. The freeze-dried product was mechanically pulverized, and 20 mg of the pulverized product was loaded on a cell culture insert (pore size: 3μm, Falcon) and immersed in the cell culture. For a control experiment, incubation was carried out in the absence of the hyaluronic acid gel composition.

Incubation conditions Plate: 12-well plate for cell culture

Medium: DMEM medium+10% fetal bovine serum, 2 ml/well

Temperature: 37.5° C. (under 5% $CO_2$)

Cell number: $1\times10^4$ cells/well

After 2, 5 and 8 days of incubation, the cell culture was examined on the cell density under an inverted microscope. As a result, it was found that the cell culture had grown in the presence of the hyaluronic acid gel composition as satisfactorily as that in the control experiment, and thereby it was ascertained that the hyaluronic acid gel composition obtained according to the present invention had no cytotoxicity.

Example 9

Sodium hyaluronate having a molecular weight of $2\times10^6$ Da and sodium carboxymethyl cellulose (manufactured by Wako Pure Chemical Industries, Ltd.) were dissolved in distilled water so that they became 0.5 mass %, respectively. The pH of this aqueous solution was adjusted with 1 mol/l hydrochloric acid to pH 1.5, to obtain an acidic aqueous solution of hyaluronic acid. 25 ml of this acidic aqueous solution of hyaluronic acid was put into a plastic petri dish and placed in a freezer set at −20° C. Freezing was carried out for 5 days to obtain a spongy hyaluronic acid gel composition. Then, this composition was immersed at 5° C. for 24 hours in 100 ml of a phosphate-buffered physiological saline of pH 7 prepared by adding a phosphate buffer component to physiological saline at a concentration of 50 mM, and neutralized, and then thoroughly washed with distilled water. And, this was freeze-dried. As a result, an adhesion preventive of the hyaluronic acid gel composition in a sheet-form, was obtained.

Example 10

Sodium hyaluronate having a molecular weight of $2\times10^6$ Da was dissolved so that it became 0.5 mass %. The pH of the prepared aqueous solution was adjusted with 1 mol/l hydrochloric acid to pH 1.5. 15 ml of the acidic aqueous solution was put into a 30 ml glass bottle and placed in a freezer set at −20° C. It was left to stand for 5 days and then unfreezed at 25° C. The obtained spongy hyaluronic acid gel was pulverized by a microhomogenizer (Polytoron, manufactured by Kinematica AG) to obtain a pulverized hyaluronic acid gel.

Sodium carboxymethyl cellulose (etherification degree: 0.62 to 0.68, calculated molecular weight: $1.28\times10^5$ to $1.35\times10^5$ Da, manufactured by Daiichi Kogyo Seiyaku Co., Ltd.) having a 1% viscosity at 25° C. of from 150 to 250 mPa·s, was dissolved in distilled water so that it became from 0.5 to 1 mass %. The pH of the aqueous solution thus prepared was adjusted with 1 mol/l nitric acid to 1.0, and 15 ml of the acidic aqueous solution was put into a 30 ml container and placed in a freezer set at −20° C. It was left to stand for 3 days and then unfreezed at 25° C. The obtained carboxymethyl cellulose gel was pulverized by a microhomogenizer (Polytoron, manufactured by Kinematica AG) to obtain a pulverized carboxymethyl cellulose gel.

The obtained pulverized hyaluronic acid gel and the sodium carboxymethyl cellulose gel were put into distilled water so that they became 10.0 mass %, respectively, followed by stirring to obtain a slurry solution. 25 ml of this slurry solution was put into a plastic petri dish of 9 cm×9 cm and naturally dried. As a result, an adhesion preventive of a hyaluronic acid gel composition in a film-form was obtained.

Comparative Example 4

In Example 9, without adjusting the pH of the mixed aqueous solution, freezing and unfreezing were repeated 8 times in a neutral state. As a result, no change of the aqueous solution of hyaluronic acid was observed. Namely, it was not gelled. This solution was put into a plastic petri dish and subjected to the 9th freezing and freeze-drying to obtain an adhesion preventive of a hyaluronic acid composition in a sheet-form.

Comparative Example 5

1.1 g of $Na_2HPO_4 \cdot 12H_2O$ was dissolved in 30 g of water and adjusted to pH 10 with 2% NaOH. To this solution, 0.3 g of sodium hyaluronate having an average molecular weight of 600,000 and 0.3 g of sodium carboxymethyl cellulose (manufactured by Wako Pure Chemical Industries, Ltd.) were dissolved in distilled water. 0.05 g of cyanuric chloride was dissolved in 0.5 ml of dioxane, then added to the above hyaluronic acid solution and reacted for 3 hours at room temperature. Then, it was put into a dialyzer and dialyzed against water for one day. 15 ml of this solution was put into a plastic petri dish and freeze-dried to obtain an adhesion preventive of a cyanuric chloride-crosslinked hyaluronic acid composition in a sheet-form.

Example 11

Test on Adhesion Preventive Effects of Adhesion Preventives of Hyaluronic Acid Gel Compositions by Means of a Mouse Uterine Model The adhesion preventives of hyaluronic acid gel compositions in sheet and film forms obtained in Examples 9 and 10 cut into 1 cm×2 cm rectangles, and as controls, the hyaluronic acid gel composition in a sheet-form obtained in Comparative Example 4 cut into a 1 cm×2 cm rectangle, and the cyanuric chloride-crosslinked hyaluronic acid composition obtained in Comparative Example 5 cut into a 1 cm×2 cm rectangle, were subjected to the following test.

7-week-old female ICR mice (body weight: 25 to 30 g) were anesthetized by intraperitoneal pentobarbital injection and cut along the ventrimeson. Then, an abrasion of about 10 cm long was made on the uterine horn of each mouse by application of iodine. Ten mice were allotted to each treatment group. The above-mentioned 1 cm×2 cm rectangular sheets of the adhesion preventives of hyaluronic acid gel compositions of Examples 9 and 10, the adhesion preventive of the hyaluronic acid composition of Comparative Example 4 and the adhesion preventive of the cyanuric chloride-crosslinked hyaluronic acid composition of Comparative Example 5, and nothing, as control, were wrapped around the abrasions. In each case, 5-0 Dexon was used for closure.

10 days later, each group of 10 mice, which were not treated or treated with the hyaluronic acid gel compositions, the hyaluronic acid composition, or the cyanuric chloride-crosslinked hyaluronic acid composition, were sacrificed by cervical dislocation. Then, ventrotomy was performed again, and inspection for adhesions was carried out. In the judgment of formation of an adhesion, very slight membranous adhesions were excluded, and only fibrous and thick adhesions strong enough not to peel off even if pulled with tweezers were counted in. The results are shown in Table 4.

TABLE 4

| Test No. | Group | Adhesion formation ratio | State of tissue | Note |
|---|---|---|---|---|
| 18 | Hyaluronic acid gel composition in Ex. 9 | 0/10 | Normal | Present invention |
| 19 | Hyaluronic acid gel composition in Ex. 10 | 0/10 | Normal | Present invention |
| 20 | Hyaluronic acid composition in Comp. Ex. 4 | 5/10 | Normal | Comparative Example |
| 21 | Not treated (physiological saline) | 9/10 | Normal | Comparative Example |
| 22 | Hyaluronic acid composition in Comp. Ex. 5 | 3/10 | Slight inflammation | Comparative Example |

As shown in Table 4, formation of adhesions was recognized in nine of the ten non-treated mice, in five of the ten treated with the hyaluronic acid composition obtained merely by freezing the hyaluronic acid mixture in a neutral state, and three of the ten treated with the cyanuric chloride-crosslinked hyaluronic acid composition, whereas the adhesion preventives of the hyaluronic acid gel composition prepared in Examples 9 and 10 developed adhesions in none of the 10 mice treated, thus indicating excellent adhesion preventive effects.

Every mouse grew normally. With respect to the state of the tissues, however, slight inflammation of the tissues was observed with the cyanuric chloride-crosslinked hyaluronic acid composition obtained in Comparative Example 5, while no abnormality was observed in the state of the tissues where the adhesion preventives of the hyaluronic acid gel compositions of Example 9 and 10 and the adhesion preventive of the hyaluronic acid composition of Comparative Example 4 were implanted.

Example 12

Sodium hyaluronate (molecular weight: $2 \times 10^5$ Da) was dissolved in distilled water so that it became 1 mass %, and the pH of the aqueous solution was adjusted with 1 mol/l nitric acid to 1.5. On the other hand, sodium carboxymethyl cellulose (etherification degree: 0.62 to 0.68, calculated molecular weight: $1.28 \times 10^5$ to $1.35 \times 10^5$ Da, manufactured by Daiichi Kogyo Seiyaku Co., Ltd.) having a 1% viscosity at 25° C. of from 150 to 250 mPa·s, was dissolved in distilled water so that it became 1 mass %, and the pH of the aqueous solution thus prepared was adjusted with 1 mol/l nitric acid to 1.5. The two acidic aqueous solutions were mixed in a volume ratio of 50:1, and 100 ml of the mixed liquid was put into a container (area: 16 cm×16 cm) and placed in a freezer set at −20° C. It was left to stand for 3 days and then unfreezed at 25° C. to obtain a spongy hyaluronic acid/carboxymethyl cellulose gel composition. Further, the obtained gel composition was washed twice with distilled water to replace an excess acid solution and then washed three times with a 100 mmol/l phosphate buffer physiological saline to carry out complete neutralization. After the neutralization, the gel was dried in air at room temperature to obtain a HA/CMC gel film.

Example 13

Sodium hyaluronate (molecular weight: $2 \times 10^5$ Da) was dissolved in distilled water so that it became 1 mass %, and the pH of the aqueous solution was adjusted with 1 N nitric acid to 1.5. On the other hand, sodium carboxymethyl cellulose (etherification degree: 0.62 to 0.68, calculated molecular weight: $1.28 \times 10^5$ to $1.35 \times 10^5$ Da, manufactured by Daiichi Kogyo Seiyaku Co., Ltd.) having a 1% viscosity at 25° C. of from 150 to 250 mPa·s, was dissolved in distilled water so that it became 1 mass %, and the pH of the aqueous solution thus prepared was adjusted with 1 mol/l nitric acid to 1.5. The two acidic aqueous solutions were mixed in a volume ratio of 2:1, and 100 ml of the mixed liquid was put into a container (area: 16 cm×16 cm) and placed in a freezer set at −20° C. It was left to stand for 3 days and then unfreezed at 25° C. to obtain a spongy hyaluronic acid/carboxymethyl cellulose gel composition. Further, the obtained gel composition was washed twice with distilled water to replace an excess acid solution, and then washed three times with a 100 mmol/l phosphate buffer physiological saline to carry out complete neutralization. After the neutralization, the gel was dried in air at room temperature to obtain a HA/CMC gel film.

Example 14

Sodium hyaluronate (molecular weight: $2 \times 10^5$ Da) was dissolved in distilled water so that it became 1 mass %, and the pH of the aqueous solution was adjusted with 1 mol/l nitric acid to 1.5. On the other hand, sodium carboxymethyl cellulose (etherification degree: 0.62 to 0.68, calculated molecular weight: $1.28 \times 10^5$ to $1.35 \times 10^5$ Da, manufactured by Daiichi Kogyo Seiyaku Co., Ltd.) having a 1% viscosity at 25° C. of from 150 to 250 mPa·s, was dissolved in distilled water so that it became 1 mass %, and the pH of the aqueous solution thus prepared, was adjusted with 1 mol/l nitric acid to 1.5. The two acidic aqueous solutions were mixed in a volume ratio of 1:1, and 100 ml of the mixed liquid was put into a container (area: 16 cm×16 cm) and placed in a freezer set at −20° C. It was left to stand for 3 days and then unfreezed at 25° C. to obtain a spongy hyaluronic acid/carboxymethyl cellulose gel composition. Further, the obtained gel composition was washed twice with distilled water to replace an excess acid solution, and then washed three times with a 100 mmol/l phosphate buffer physiological saline to carry out complete neutralization. After the neutralization, the gel was dried in air at room temperature to obtain a HA/CMC gel film.

Example 15

Sodium hyaluronate (molecular weight: $2 \times 10^5$ Da) was dissolved in distilled water so that it became 1 mass %, and the pH of the aqueous solution was adjusted with 1 mol/l nitric acid to 1.5. On the other hand, sodium carboxymethyl cellulose (etherification degree: 0.62 to 0.68, calculated molecular weight: $1.28 \times 10^5$ to $1.35 \times 10^5$ Da, manufactured by Daiichi Kogyo Seiyaku Co., Ltd.) having a 1% viscosity at 25° C. of from 150 to 250 mPa·s, was dissolved in distilled water so that it became 1 mass %, and the pH of the aqueous solution thus prepared, was adjusted with 1 mol/l nitric acid to 1.5. The two acidic aqueous solutions were mixed in a volume ratio of 1:2, and 100 ml of the mixed liquid was put into a container (area: 16 cm×16 cm) and placed in a freezer set at −20° C. It was left to stand for 3 days and then unfreezed at 25° C. to obtain a spongy hyaluronic acid/carboxymethyl cellulose gel composition. Further, the obtained gel composition was washed twice with distilled water to replace an excess acid solution, and then washed three times with a 100 mmol/l phosphate buffer physiological saline to carry out complete neutralization. After the neutralization, the gel was dried in air at room temperature to obtain a HA/CMC gel film.

Example 16

Sodium hyaluronate (molecular weight: $2 \times 10^5$ Da) was dissolved in distilled water so that it became 1 mass %, and the pH of the aqueous solution was adjusted with 1 mol/l nitric acid to 1.5. On the other hand, sodium carboxymethyl cellulose (etherification degree: 0.62 to 0.68, calculated molecular weight: $1.28 \times 10^5$ to $1.35 \times 10^5$ Da, manufactured by Daiichi Kogyo Seiyaku Co., Ltd.) having a 1% viscosity at 25° C. of from 150 to 250 mPa·s, was dissolved in distilled water so that it became 1 mass %, and the pH of the aqueous solution thus prepared, was adjusted with 1 mol/l nitric acid to 1.5. The two acidic aqueous solutions were mixed in a volume ratio of 50:1, and 100 ml of the mixed liquid was put into a container (area: 16 cm×16 cm) and placed in a freezer set at −20° C. It was left to stand for 3 days and then unfreezed at 25° C. to obtain a spongy hyaluronic acid/carboxymethyl cellulose gel composition. Further, the obtained gel composition was washed twice with distilled water to replace an excess acid solution, and then washed three times with a 100 mmol/l phosphate buffer physiological saline to carry out complete neutralization. After the neutralization, the gel was freezed to obtain a HA/CMC gel sheet.

Example 17

Sodium hyaluronate (molecular weight: $2 \times 10^5$ Da) was dissolved in distilled water so that it became 1 mass %, and the pH of the aqueous solution was adjusted with 1 mol/l nitric acid to 1.5. On the other hand, sodium carboxymethyl cellulose (etherification degree: 0.62 to 0.68, calculated molecular weight: $1.28 \times 10^5$ to $1.35 \times 10^5$ Da, manufactured by Daiichi Kogyo Seiyaku Co., Ltd.) having a 1% viscosity at 25° C. of from 150 to 250 mPa·s, was dissolved in distilled water so that it became 1 mass %, and the pH of the aqueous solution thus prepared, was adjusted with 1 mol/l nitric acid to 1.5. The two acidic aqueous solutions were mixed in a volume ratio of 2:1, and 100 ml of the mixed liquid was put into a container (area: 16 cm×16 cm) and placed in a freezer set at −20° C. It was left to stand for 3 days and then unfreezed at 25° C. to obtain a spongy hyaluronic acid/carboxymethyl cellulose gel composition. Further, the obtained gel composition was washed twice with distilled water to replace an excess acid solution, and then washed three times with a 100 mmol/l phosphate buffer physiological saline to carry out complete neutralization. After the neutralization, the gel was freezed to obtain HA/CMC gel sheet.

Example 18

Sodium hyaluronate (molecular weight: $2 \times 10^5$ Da) was dissolved in distilled water so that it became 1 mass %, and the pH of the aqueous solution was adjusted with 1 mol/l nitric acid to 1.5. On the other hand, sodium carboxymethyl cellulose (etherification degree: 0.62 to 0.68, calculated molecular weight: $1.28 \times 10^5$ to $1.35 \times 10^5$ Da, manufactured by Daiichi Kogyo Seiyaku Co., Ltd.) having a 1% viscosity at 25° C. of from 150 to 250 mPa·s, was dissolved in distilled water so that it became 1 mass %, and the pH of the aqueous solution thus prepared, was adjusted with 1 mol/l nitric acid to 1.5. The two acidic aqueous solutions were mixed in a volume ratio of 1:1, and 100 ml of the mixed liquid was put into a container (area: 16 cm×16 cm) and placed in a freezer set at −20° C. It was left to stand for 3 days and then unfreezed at 25° C. to obtain a spongy hyaluronic acid/carboxymethyl cellulose gel composition. Further, the obtained gel composition was washed twice with distilled water to replace an excess acid solution, and then washed three times with a 100 mmol/l phosphate buffer physiological saline to carry out complete neutralization. After the neutralization, the gel was freezed to obtain HA/CMC gel sheet.

Example 19

Sodium hyaluronate (molecular weight: $2 \times 10^5$ Da) was dissolved in distilled water so that it became 1 mass %, and the pH of the aqueous solution was adjusted with 1 mol/l nitric acid to 1.5. On the other hand, sodium carboxymethyl cellulose (etherification degree: 0.62 to 0.68, calculated molecular weight: $1.28 \times 10^5$ to $1.35 \times 10^5$ Da, manufactured by Daiichi Kogyo Seiyaku Co., Ltd.) having a 1% viscosity at 25° C. of from 150 to 250 mPa·s, was dissolved in distilled water so that it became 1 mass %, and the pH of the aqueous solution thus prepared, was adjusted with 1 mol/2 nitric acid to 1.5. The two acidic aqueous solutions were mixed in a volume ratio of 1:2, and 100 ma of the mixed liquid was put into a container (area: 16 cm×16 cm) and placed in a freezer set at −20° C. It was left to stand for 3 days and then unfreezed at 25° C. to obtain a spongy hyaluronic acid/carboxymethyl cellulose gel composition. Further, the obtained gel composition was washed twice with distilled water to replace an excess acid solution, and then washed three times with a 100 mmol/l phosphate buffer physiological saline to carry out complete neutralization. After the neutralization, the gel was freezed to obtain HA/CMC gel sheet.

Example 20
Solubility Tests of Hyaluronic Acid/carboxymethyl Cellulose Gel Compositions A phosphate buffer component was added to physiological saline at a concentration of 50 mmol/2 to obtain a phosphate buffered physiological saline of pH 7.4. The gel compositions on a dry weight of 50 ml obtained in the preceding Examples 11 to 18 were immersed in the phosphate-buffered physiological saline in such a proportion that they were in 50 ml of the phosphate-buffered physiological saline. Further, the proportions of the hyaluronic acid and the carboxymethyl cellulose eluting into the phosphate-buffered physiological saline at 37° C. were obtained from the hyaluronic acid concentration in the phosphate-buffered physiological saline.

Accordingly, the solubility of a hyaluronic acid gel composition in a neutral aqueous solution at 37° C. is one prescribed by the above test.

Measurement of Hyaluronic Acid and Carboxymethyl Cellulose Concentrations

After completely decomposing the gel by an addition of a NaOH solution, hyaluronic acid in the phosphate-buffered physiological saline was subjected to hyaluronic acid splitting enzyme treatment. And, the sample for analysis was filtered through a 0.45 μm filter and then measured by means of GPC. The concentrations of hyaluronic acid and the carboxymethyl cellulose were obtained from a peak area of the peak of hyaluronic acid thus eluted, as measured by a differential refractometer. The hyaluronic acid has a molecular weight lowered by the enzymatic splitting, and thus peak separation from the carboxymethyl cellulose having a high molecular weight, is possible.

As described above, the solubility tests of the hyaluronic acid gel compositions of Examples 12 to 19 were specifically carried out. The results are shown in Tables 5 and 6.

TABLE 5

Solubility of hyaluronic acid gel (pH 7)

| Test No. | Form | Composition | 1 day | 3 days | 7 days | Note |
|---|---|---|---|---|---|---|
| 23 | Film-form | 50:1 | 96 | 81 | 74 | Ex. 12 |
| 24 | | 2:1 | 96 | 90 | 62 | Ex. 13 |
| 25 | | 1:1 | 95 | 93 | 67 | Ex. 14 |
| 26 | | 1:2 | 97 | 87 | 68 | Ex. 15 |
| 27 | Sheet-form | 50:1 | 94 | 82 | 70 | Ex. 16 |
| 28 | | 2:1 | 94 | 86 | 72 | Ex. 17 |
| 29 | | 1:1 | 95 | 87 | 59 | Ex. 18 |
| 30 | | 1:2 | 97 | 81 | 65 | Ex. 19 |

TABLE 6

Solubility of hyaluronic acid gel (pH 8)

| Test No. | Form | Composition | 1 day | 3 days | 7 days | Note |
|---|---|---|---|---|---|---|
| 31 | Film-form | 50:1 | 70 | 46 | 27 | Ex. 12 |
| 32 | | 2:1 | 64 | 42 | 22 | Ex. 13 |
| 33 | | 1:1 | 72 | 53 | 20 | Ex. 14 |
| 34 | | 1:2 | 83 | 50 | 19 | Ex. 15 |
| 35 | Sheet-form | 50:1 | 72 | 44 | 20 | Ex. 16 |
| 36 | | 2:1 | 69 | 43 | 22 | Ex. 17 |
| 37 | | 1:1 | 73 | 49 | 25 | Ex. 18 |
| 38 | | 1:2 | 71 | 41 | 21 | Ex. 19 |

From Tables 5 and 6, it was evident that with the gel compositions having any compositional ratios, by gelation, both hyaluronic acid and the carboxymethyl cellulose became hardly soluble.

Example 21
Test on Cytotoxicity of the Hyaluronic Acid Gel Composition

The cytotoxicity of the hyaluronic acid gel composition obtained according to the present invention was evaluated by observing the proliferation behavior of a normal human skin-derived fibroblast culture in the presence of the hyaluronic acid gel composition obtained according to the present invention without contact between them. The gel composition prepared by the method in Examples 12 to 19 was mechanically pulverized, and 20 mg of the pulverized gel was loaded on a cell culture insert (pore size: 3 μm, Falcon) and immersed in the cell culture. For a control experiment, incubation was carried out in the absence of the hyaluronic acid gel composition.

Incubation conditions Plate: 12-well plate for cell culture

Medium: DMEM medium+10% fetal bovine serum, 2 ml/well

Temperature: 37.5° C. (under 5% $CO_2$)

Cell number: $1\times10^4$ cells/well

After 2, 5 and 8 days of incubation, the cell culture was examined on the cell density under an inverted microscope. As a result, it was found that the cell culture had grown in the presence of the gel composition as satisfactorily as that in the control experiment, and thereby it was confirmed that the gel composition obtained according to the present invention had no cytotoxicity.

Example 22
Adhesion Preventive Test on a Rat Appendix Model

Adhesion Inducing Method

A rat (SD, female, at least 9 weeks old) was anesthetized by intramuscular injection of an anesthetic to its lower limb and fixed on its back. After disinfecting the abdominal skin with isodine, shaving hair was carried out. The abdominal muscle of the rat was cut along the ventrimeson. The appendix was abraded by pressing a rotating rod covered with a gauge. The film-form adhesion preventive prepared from the hyaluronic acid composition as the material was placed at the abraded portion, and the appendix was returned to the initial position, followed by suturing. One having the appendix returned to the initial position without applying the adhesion preventive was used as control. Ten rats were used for each test including the control.

About one week after the operation, ventrotomy was performed, and inspection for adhesions was carried out. In the judgment of formation of an adhesion, very slight membranous adhesions were excluded, and only fibrous and thick adhesions strong enough not to peel off even if pulled with tweezers were counted in. The results are shown in Table 7.

Further, 200 ml/81 $cm^2$ of the compositions prepared in Comparative Examples 4 and 5 and Examples 14 to 16 as test specimens, the effects as adhesion preventives were evaluated in accordance with the above method.

TABLE 7

Test on adhesion preventive of the hyaluronic acid gel

| Test No. | Group | Adhesion formation ratio | State of tissue | Note |
|---|---|---|---|---|
| 39 | Not treated | 9/10 | Normal | Comparative Example |
| 40 | Hyaluronic acid composition in Comp. Ex. 4 | 7/10 | Normal | Comparative Example |
| 41 | Hyaluronic acid composition in Comp. Ex. 5 | 4/10 | Slight inflammation | Comparative Example |
| 42 | Hyaluronic acid composition in Ex. 14 | 3/10 | Normal | Present invention |
| 43 | Hyaluronic acid composition in Ex. 15 | 2/10 | Normal | Present invention |
| 44 | Hyaluronic acid composition in Ex. 16 | 2/10 | Normal | Present invention |

As shown in Table 7, formation of adhesions was recognized in nine of the ten non-treated rats, in seven of the ten treated with the hyaluronic acid composition obtained merely by freezing the hyaluronic acid mixture in a neutral state, and in four of the ten treated with the cyanuric chloride-crosslinked hyaluronic acid composition, whereas the adhesion preventive of the hyaluronic acid gel composition prepared in Example 8 developed adhesions in three or less of the ten rats treated, thus indicating excellent adhesion preventive effects.

With respect to the states of the tissues, slight inflammation of the tissue was observed with the cyanuric chloride-crosslinked hyaluronic acid composition obtained in Comparative Example 5, while no abnormality was observed in the states of the tissues where the adhesion preventives of the cyanuric acid gel compositions of Examples 14 to 16 and the adhesion preventive of the cyanuric acid composition of Comparative Example 4, were implanted.

Example 23

Test on wound treating effects of the gel wound dressing by means of a rat apellous model The hair at the back of a Winstar female rat of 7 weeks old (about 200 g) was shaved, and by means of ophthalmic scissors, the back skin portion was taken off in a circle shape with a diameter of 2 cm under anesthesia with ether, to prepare a complete apellous wound. A non-treated group having only medical non-woven gauzes (40×40 mm: double layered) applied, and treated groups having compositions (30×30 mm) prepared in Comparative Examples 4 and 5 and Example 14 covered on the wound surfaces and having medical non-woven gauzes (40×40 mm: double layered) applied, were set. Six rats were used for each group. The medical non-woven gauzes were set by an adhesive dressing and further fixed by taping.

The curing effects were compared by measuring the change with time of the wound area. Namely, the area ratio to the initial wound area is obtained by the following formula, and its change in time was examined.

The results are shown in Table 8.

Area ratio (%)={(long diameter×short diameter of the wound area on the inspection day)/(long diameter×diameter of the initial wound area)}×100

TABLE 8

Test on wound curing effects of hyaluronic acid gel

| Test No. | Test groups | Area ratio (%) | | | | |
|---|---|---|---|---|---|---|
| | | 0 day | 2 days | 3 days | 7 days | 10 days |
| 45 | Not treated | 100 | 93 | 81 | 74 | 65 |
| 46 | Hyaluronic acid composition in Comp. Ex. 4 | 100 | 93 | 75 | 65 | 57 |
| 47 | Hyaluronic acid composition in Comp. Ex. 5 | 100 | 89 | 74 | 60 | 49 |
| 48 | Hyaluronic acid composition in Ex. 14 | 100 | 86 | 74 | 45 | 35 |

From Table 8, it was evident that the hyaluronic acid gel sheets which became hardly water-soluble, increased the wound curing effects.

Example 24

Sodium hyaluronate having a molecular weight of $2 \times 10^6$ Da was dissolved in distilled water so that it became 0.5 mass %. The pH of the prepared aqueous solution was adjusted with 1 mol/l hydrochloric acid to pH 1.5. 15 ml of the acidic aqueous solution was put into a 30 ml glass bottle and placed in a freezer set at −20° C. It was left to stand for 5 days and then unfreezed at 25° C. The obtained spongy hyaluronic acid gel was pulverized by a microhomogenizer (Polytoron, manufactured by Kinematica AG) to obtain a pulverized hyaluronic acid gel. The pulverized hyaluronic acid gel was dispersed in a solution having sodium carboxymethyl cellulose (manufactured by Wako Pure Chemical Industries, Ltd.) dissolved in distilled water in an amount of 1.0 mass %, so that it became 2.0 mass %. 25 ml of this solution was put into a plastic petri dish of 9 cm×9 cm and naturally dried. As a result, a hyaluronic acid gel composition in a film-form was obtained.

Example 25

In the same manner as in Example 1, a pulverized hyaluronic acid gel was obtained. The pulverized hyaluronic acid gel was dispersed in a solution having polyvinyl alcohol (polymerization degree: 1,500, manufactured by Wako Pure Chemical Industries, Ltd.) dissolved in distilled water in an amount of 1.0 mass %, so that it became 2.0 mass %. 25 ml of this solution was put into a plastic petri dish of 9 cm×9 cm and naturally dried. As a result, a hyaluronic acid gel composition in a film-form was obtained.

Example 26

In the same manner as in Example 1, a pulverized hyaluronic acid gel was obtained. The pulverized hyaluronic acid gel was dispersed in a solution having gelatin (manufactured by Funakoshi K.K.) dissolved in distilled water in an amount of 1.0 mass %, so that it became 2.0 mass %. 25 ml of this solution was put into a plastic petri dish of 9 cm×9 cm and naturally dried. As a result, a hyaluronic acid gel composition in a film-form was obtained.

Example 27

In the same manner as in Example 1, a pulverized hyaluronic acid gel was obtained. The pulverized hyaluronic acid gel was dispersed in a solution having chondroitin (manufactured by Wako Pure Chemical Industries, Ltd.) dissolved in distilled water in an amount of 1.0 mass %, so that it became 2.0 mass %. 25 ml of this solution was put into a plastic petri dish of 9 cm×9 cm and naturally dried. As a result, a hyaluronic acid gel composition in a film-form was obtained.

Comparative Example 6

In the same manner as in Example 1, a pulverized hyaluronic acid gel was obtained. The obtained pulverized hyaluronic acid gel was dispersed in distilled water so that it became 3.0 mass %. 25 ml of this solution was put into a plastic petri dish of 9 cm×9 cm and naturally dried. As a result, a hyaluronic acid gel composition in a film-form was obtained.

Example 28

Test on Dry Strength of the Hyaluronic Acid Gel Compositions

The dry tensile strength of the film-form hyaluronic acid gel compositions and hyaluronic acid gel in the preceding Examples 24 to 27 and Comparative Example 6, was measured by EZ-TEST manufactured by Shimadzu Corporation. Each sample was cut into a rectangular shape of 1 cm×5 cm, and the maximum stress at the time of tensile breakage at a crosshead speed of 10 mm/min with a distance of 30 mm, was measured.

The results are shown in Table 9. The loads at the time of breakage of the films of the hyaluronic acid gel compositions of Examples 24 to 27 are larger than the film made solely of the hyaluronic acid gel of Comparative Example 6, thus indicating improvement of the dry strength.

TABLE 9

Dry strength of the hyaluronic acid gel compositions

| Test No. | Dry strength (MPa) | Note |
| --- | --- | --- |
| 49 | 59 | Example 24 |
| 50 | 65 | Example 25 |
| 51 | 52 | Example 26 |
| 52 | 65 | Example 27 |
| 53 | 45 | Comparative Example 6 |

Example 29

Test on Tissue Bondability of the Hyaluronic Acid Gel Compositions

The tissue bondability of the film-form hyaluronic acid gel compositions and hyaluronic acid gel in the preceding Examples 24 to 27 and Comparative Example 6, was measured by EZ-TEST manufactured by Shimadzu Corporation.

Each sample was cut into a square of 1 cm×1 cm, and mounted on a crosshead, and the stress at the time of peeling from a skinless chicken as a tissue, was measured. Each sample and the tissue were brought in contact for 30 seconds under a pressure of 0.01 kg/cm$^2$, and then the maximum stress at the time of pulling and peeling at a crosshead speed of 1 mm/min with a distance of 30 mm, was measured.

The results are shown in Table 10.

TABLE 10

Tissue bondability of the hyaluronic acid gel compositions

| Test No. | Maximum peeling load (N) | Note |
| --- | --- | --- |
| 54 | 2.0 | Example 24 |
| 55 | 1.5 | Example 25 |
| 56 | 1.7 | Example 26 |
| 57 | 1.9 | Example 27 |
| 58 | 0.9 | Comparative Example 6 |

From Table 10, the loads at the time of breakage of the films of the hyaluronic acid gel compositions of Examples 24 to 27 are superior to that of the film of the hyaluronic acid gel of Comparative Example 6.

INDUSTRIAL APPLICABILITY

As described in the foregoing, according to the present invention, a hyaluronic acid gel composition comprising hyaluronic acid and a polymer, can be prepared simply without using any chemical cross-linking agent or chemical modifying agent. And, this hyaluronic acid gel composition supplements various physical properties of the gel formed solely of hyaluronic acid and further can be presented as a medical material which is excellent in biocompatibility and which is useful in the medical field.

What is claimed is:

1. A composition comprising:

hyaluronic acid and a polymer, wherein said composition has a percentage dissolution of hyaluronic acid of 50% or lower in 12 hours in a neutral aqueous solution of 37° C. and wherein said composition is produced by a process that does not require the use of cross-liking agents or chemical modifying agents to achieve the percentage dissolution of hyaluronic acid of 50% or lower in 12 hours in a neutral aqueous solution of 37° C.

2. The hyaluronic acid gel composition of claim 1, wherein the polymer is carboxymethyl cellulose.

3. A process for producing a hyaluronic acid gel composition comprising:

freezing an aqueous solution or dispersion having a pH of 3.5 or lower and comprising hyaluronic acid and a polymer and unfeezing said aqueous solution or dispersion to form a hyaluronic acid gel composition.

4. A process for producing a hyaluronic acid gel composition comprising:

freezing an aqueous solution having a pH of 3.5 or lower and comprising hyaluronic acid, unfreezing said solution to form a hyaluronic acid gel, and mixing the hyaluronic acid gel with a polymer or a polymer gel to form a hyaluronic acid gel composition.

5. The process of claim 3, wherein said polymer comprises at least one substance selected from the group Consisting of a polysaccharide, protein, nucleic acid and synthetic polymer.

6. The process of claim 3, wherein the polymer is carboxymethyl cellulose.

7. A material comprising the composition of claim 1.

8. A material comprising a hyaluronic acid gel composition which is obtained by irradiating, or injecting, a hyaluronic acid gel composition with at least one member selected from the group consisting of gamma rays, electron rays, plasma and EOG (ethylene oxide gas).

9. The material of claim 7, wherein the material is an adhesion preventive.

10. The material according to claim 7, wherein the material is a wound dressing.

11. The process of claim 4, wherein the polymer is at least one substance selected from the group consisting of a polysaccharide, protein, nucleic acid and synthetic polymer.

12. The process of claim 4, wherein the polymer is carboxymethyl cellulose.

13. A material comprising the hyaluronic acid gel composition of claim 2.

14. The material of claim 13, wherein the material is an adhesion preventive.

15. The material of claim 13, wherein the material is a wound dressing.

16. The composition of claim 1, wherein said polymer comprises one or more polymers selected for a the group consisting of polysaccharide(s), protein(s), nucleic acid(s) and synthetic polymer(s).

17. The composition of claim 1, wherein said polymer comprises a polysaccharide.

18. The composition of claim 1, wherein said polymer comprises a protein.

19. The composition of claim 1, wherein said polymer comprises a nucleic acid.

20. The composition of claim 1, wherein said polymer comprises a synthetic polymer.

21. The composition of claim 1, wherein said polymer comprises carboxymethyl cellulose.

22. The composition of claim 1, wherein the hyaluronic acid is extracted from animal tissue.

23. The composition of claim 1, wherein the hyaluronic acid is produced by fermentation.

24. The composition of claim 1, wherein the hyaluronic acid has a molecular weight ranging from about $1 \times 10^5$ to about $1 \times 10^7$ Da.

25. The composition of claim 1 in a molded form.

26. The composition of claim 1 in sheet-form, film-form, pulverized form, sponge-form, bulk-form, fiber-form, fluid-form or tube-form.

27. A medical material comprising the composition of claim 1.

28. The composition of claim 27 that has been treated with gamma rays, electron rays, plasma or EOG (ethylene oxide gas).

29. The composition of claim 1 that is artificial cartilege, a carrier for a pharmacologically active substance, artificial skin, a replacement vital tissue repairer, a joint injection, a surgical suture, a hemostatic material, an artificial organ, artificial extracellular matrix, artificial basement membrane, a medical tool or a medical device.

30. A wound dressing comprising the composition of claim 1.

31. An adhesion preventative comprising the composition of claim 1.

* * * * *